BEST AVAILABLE COPY

United States Statutory Invention Registration [19]

[11] Reg. Number: H919

Marsella

[43] Published: May 7, 1991

[54] PROCESS FOR PRODUCING POLYAMINE BORANES

[76] Inventor: John A. Marsella, 744 N. Broad St., Allentown, Pa. 18104

[21] Appl. No.: 388,540

[22] Filed: Aug. 2, 1989

[51] Int. Cl.[5] ..... C07C 69/76
[52] U.S. Cl. ..... 564/8
[58] Field of Search ..... 564/8

[56] References Cited

U.S. PATENT DOCUMENTS

| | | | |
|---|---|---|---|
| 2,927,133 | 3/1960 | Bragdon | 564/8 X |
| 3,013,016 | 12/1989 | Haberland et al. | 260/313 |
| 3,094,562 | 6/1963 | Ashby | 564/8 |
| 3,317,525 | 5/1967 | Swover | 564/8 X |

FOREIGN PATENT DOCUMENTS

| | | |
|---|---|---|
| 242064 | 8/1985 | Czechoslovakia . |
| 909390 | 10/1962 | United Kingdom . |

OTHER PUBLICATIONS

Taylor, M. D.,; Grant, L. R.; and Clifton A. Sands, "A Convenient Preparation of Pyridine-Borane" J. Am. Chem., vol. 77, 1955, pp. 1506-1507.

*Primary Examiner*—John Maples
*Assistant Examiner*—Joseph Anthony

[57] ABSTRACT

This invention relates to a process for producing tertiarydiamine-boranes by reacting a tertiary diamine with a borohydride in the presence of a carboxylic or mineral acid source. Water is included in the reaction medium in a catalytic amount but insufficient for forming two phases. Excellent selectivity to tertiary diamine-boranes is achieved.

11 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR PRODUCING POLYAMINE BORANES

TECHNICAL FIELD

This invention relates to a process for producing tertiary polyamine boranes by the reaction of a borohydride with a tertiary polyamine.

BACKGROUND OF THE INVENTION

Tertiary amine boranes are utilized in many fields, which include the preparation of epoxy resins by acting as a curing agent or accelerators; in organic synthesis as reducing agent; as a reagent for the hydroboration of alkenes and in electroless plating applications. Essentially five methods have been developed for the synthesis of tertiary amine-boranes and these methods are described as follows:

1. The direct reaction of an amine and diborane;
2. Reacting tetrahydroborates with ammonium salts;
3. Transamination of aminoboranes;
4. The reaction of a metal tetrahydroborate with iodine in the presence of an amine; and
5. The reaction of a metal tetrahydroborate with carbon dioxide or carboxylic or mineral acid in the presence of an amine and organic solvent.

Many of the above methods were difficult to practice in the production of tertiary amine-boranes because of the required synthesis of various reactive materials, the handling of expensive or difficult to handle reagents and difficulty in product recovery.

Of the above synthesis techniques, the one which appears to be most widely utilized is synthesis route 5 which involves the reaction of a metal borohydride with a tertiary amine. The following patents are representative:

U.S. Pat. No. 3,013,016 discloses a process embraced within synthesis route 5 for producing trialkylamine boranes. A trialkylamine, e.g. trimethylamine or triethylamine, is contacted with potassium borohydride in the presence of an aqueous phase containing an inert organic solvent which is immiscible or only partially miscible with water. Carbon dioxide, or an acid source such as a carboxylic acid or mineral acid is added to the reaction medium. Reaction occurs at about 20°–40° C. and atmospheric pressure. The product is recovered by separating the organic solution containing the trialkylamine borane for the aqueous phase and then separating the organic solvent from the trialkylamine borane by distillation.

Czechoslovakian patent 242,064 discloses a process for producing tertiary amine-boranes via synthesis route 5 wherein an anhydrous suspension of a metal tetrahydroborate and tertiary amine in an organic solvent is contacted with carbon dioxide gas at temperatures ranging from about 0° to 50° C. for a period of 1–5 hours. The reaction product is washed with water, dried and the solvent evaporated.

British patent 909,390 discloses a process for producing amine boranes by reacting an amine salt with aqueous metal borohydride in organic solvent at room temperature under neutral or alkaline conditions. Product recovery is accomplished by separating the amine borane as it is formed by separating organic solvent containing the amine borane from the aqueous layer and then distilling the solvent from the amine borane.

Taylor, et al. in J. Am. Chem. Soc., vol. 77, 1955, pp. 1506–7 disclose the production of pyridine-borane complexes by reacting pyridine hydrochloride with sodium borohydride in the presence of pyridine solvent. By-product sodium chloride precipitates and unreacted pyridine hydrochloride is precipitated by the addition of ether. Unreacted pyridine is separated from the pyridine-borane reaction product by distillation.

SUMMARY OF THE INVENTION

This invention relates to an improved process for preparing amine boranes by the reaction of a metal borohydride with a tertiary amine in the presence of an inert, water immiscible organic solvent and a protic acid source. The improvement for enhancing yields in the production of the amine borane complexes having a water solubility greater than about 2 grams per 100 cc's at 25° C. and where the amine is a polyamine containing at least one tertiary nitrogen atom comprises effecting the reaction of the borohydride with the complex in the presence of water, wherein the water is present in a small but catalytically effective amount but insufficient for forming two phases. There are several advantages associated with the process of this invention. These advantages include:

an ability to produce tertiary amine-borane in high yield;

an ability to produce a commercially desirable white solid as product;

an ability to produce tertiary amine-boranes in a one-pot synthesis approach, and an ability to separate the product from the reaction mixture with relative ease.

DETAILED DESCRIPTION OF THE INVENTION

In the conventional preparation of tertiary amine boranes, a tertiary amine or salt is reacted with a borohydride under modest reaction conditions. In this case the tertiary amines are polyamines containing a tertiary nitrogen atom, e.g., diamines having from about 2–10 carbon atoms, which may be aliphatic or cyclic. Examples of tertiary amines include N-alkylated polyamines, e.g. methylated and ethylated derivatives of polyamines such as, ethylenediamine, propylenediamine, diethylenetriamine and triethylenetetraamine, e.g., methylated ethylenediamine or methylated propanediamine and methylated triethylenetetramine; cyclic amines, e.g. dimethylpiperazine, diethylpiperazine, triethylenediamine and methyltriethylenediamine; and ether amines, e.g., dimethylaminoethyl ether and bis morpholinoethyl ether. Of these polyamines, triethylenediamine and methyl-triethylenediamine are well suited for forming borane complexes.

The borohydrides which are reacted with the tertiary amine include alkali metal borohydrides such as sodium borohydride and potassium borohydride and lithium borohydride. Borane may also be used.

To facilitate reaction between the tertiary amine and borohydride, the reactants are dissolved in an organic solvent which is inert to the reaction medium. Conventional organic solvents, which are suited for producing tertiary amine boranes include hydrocarbons such as benzene, toluene, xylene; ethers such as diethylether, methodyethylether, dimethoxyethane, methyltert-butylether, dioxane, tetrahydrofuran and isopropyl ether; aliphatic hydrocarbons, i.e., those having from about 6 to 20 carbon atoms, e.g., hexane, pentane, dodecane, and the like. In addition various carboxylic esters

BEST AVAILABLE COPY

BEST AVAILABLE COPY such as ethylacetate, propylacetate and the like and nitriles such as acetonitrile can be used. The organic solvents used in the synthesis are well known and most will work so long as the reactant amine and product borane complex are soluble in the solvent and sufficiently volatile such that they can be distilled away from the reaction product.

The reaction of the tertiary amine with the alkali metal borohydride is carried out in the presence of a protic acid source, e.g. a $C_{2-10}$, preferably a $C_2$–$C_4$ carboxylic acid, or an anhydrous mineral acid. Examples of $C_{2-10}$ carboyxlic acid sources include, acetic acid, propionic acid, butyric acid and examples of mineral acids include hydrochloric, phosphoric and sulfuric acids. When using a mineral acid it may be necessary to dilute such acids in an organic solvent as the anhydrous, concentrated mineral acids may be too strong and cause product decomposition.

In contrast to previous processes, the reaction is carried out in the presence of only a trace amount of water, i.e., sufficient water to catalytically enhance the production of the tertiary amine borane complex but insufficient for forming two phases, e.g. the saturation level. Typically, the level of water will range from at least about 0.5% based on the weight of the solvent to the saturation point of water in the solvent. This may be from 1.2% for ethyl ether to 0.6% for isopropyl ether to 1.5% for tert-butyl ether to 3.3% for ethyl acetate. In contrast to the prior art processes water is to be avoided in the reaction and in product recovery in order to maximize the yield of tertiary amine boranes produced and to facilitate the recovery of the tertiary amine borane from the reaction medium. When excess water is present in the reaction medium, as evidenced by two phases with the water immiscible organic solvent, yields typically drop because of movement of the tertiary amine borane from the organic solvent to the aqueous phase thus resulting in product loss. Although not intending to be bound by theory it is believed that the tertiary polyamine or diamine results in a more water soluble product than does the monoamine borane and when present in a carboxylic acid containing aqueous medium the tertiaryamine borane is destroyed.

Temperatures required for reaction of the tertiary amine with the alkali metal borohydride are conventional and typically range from about −25° to 30° C., preferably −15° to 15° C., with pressures ranging from atmospheric to 50 psig.

The following examples are provided to illustrate embodiments of the invention and are not an attempted to restrict the scope thereof.

EXAMPLE 1

Methyl-triethylenediamine (MTEDA) Borane In Presence of Water and an acetic acid suspension of 20 g $NaBH_4$ in 375 mL anhydrous diethyl ether (specified as containing <0.01% water) was cooled to 2° C. in a cooling bath. To this was added 61.5 g of freshly distilled methyl-triethylenediamine (MTEDA, water content 600 ppm) and 1.5 mL $H_2O$. A solution of 30 g glacial acetic acid (99.7) in 30 mL anhydrous diethyl ether was added to the stirred suspension at such a rate that the addition was complete in 70 minutes and the reaction temperature did not exceed 5° C. The mixture was stirred an additional 40 min. at <5° C. and the cooling bath was then removed. Stirring was continued an additional 45 min. as the temperature rose to 18° C. The reaction mixture was then allowed to stand overnight. At this time, the mixture was filtered and the ether solution was removed to give 24.4 g of MTEDA/$BH_3$ which was obtained as a white solid. The remaining solid from the filtration was washed thoroughly with toluene and the wash solution was taken to dryness to yield an additional 37 g of product. A product yield of about 87% was obtained.

EXAMPLE 2

Preparation of Methyl-triethylenediamine Borane in Presence of Acetic Acid and water containing methyl-triethylenediamine Approximately 200 mL anhydrous $Et_2O$ was placed in a flask and the flask was purged with $N_2$ for ~15 minutes. To this was added 19 g $NaBH_4$. The mixture was cooled to 0° C. with an ice bath and 63 g of crude MTEDA (~2.5% $H_2O$ content) was carefully added while observing the temperature. A solution of 30 g of glacial acetic acid in 30 mL anhydrous ethyl ether was prepared and placed in an addition funnel that was then placed on the flask. The amount of ether in the reaction flask was then adjusted so that it was approximately 250 mL. The acetic acid solution was slowly added, while stirring vigorously, over a period of 75 minutes at such a rate so as to maintain the reaction temperature at 3°–7° C. Vigorous gas evolution was noted. After the addition was complete, the temperature fell and the gas evolution slowed. Stirring was continued for 30 minutes and the temperature was slowly raised to room temperature. The flask was kept under a slow $N_2$ purge overnight. The next day, the solid residue was extracted with a total of 800 mL ether and 600 mL toluene. The extracts were dried to give a total of 62.5 g of waxy yellow solid (89% yield). This procedure gave yields of 69–92% (five runs) on this scale and 79–88% (four runs) when run at twice the scale. Yields were excellent.

This example shows that trace amounts of water can be added to the reaction medium by addition with the methyl-triethylenediamine feed in contrast to being added as a separate component as illustrated in Example 1.

EXAMPLE 3

Preparation of Methyl-triethylenediamine in Presence of Acetic Acid in Anhydrous Medium The procedure of Example 1 was repeated except that the 1.5 ml $H_2O$ water addition was omitted. Glacial acetic acid was used as the protic acid source. A clear, colorless, liquid, as opposed to the white solid obtained in Example 1 was obtained. The liquid product was analyzed by $^{13}C$ NMR and analysis showed the liquid consisted of a 1:1 mixture of a methyl-triethylenediamine/$BH_3$ complex and an acetyl containing impurity.

EXAMPLE 4

Preparation of Methyl-triethylenediamine Borane in Presence of $CO_2$ in Anhydrous Medium Methyl-triethylenediamine (63 grams) was charged to a vessel along with a suspension of 19.5 grams sodium borohydride in 300 mL's anhydrous acetonitrile. Carbon dioxide was bubbled through the suspension, while stirring, for about 90 minutes. The temperature was maintained at 20°–25° C. during the reaction period. A white product was obtained in about 87% yield.

BEST AVAILABLE COPY

This example, in contrast to Example 3, showed that $CO_2$ was effective for effecting the reaction between methyl-triethylenediaine and sodium borohydride in an anhydrous medium while the protic acid, glacial acetic acid, was ineffective. The by-product acetyl containing impurity was not present when $CO_2$ was used as the reactant and it was concluded the reaction was by a different mechanism than that when protic acid was used.

EXAMPLE 5

Preparation of Methyl-Triethylenediamine Borane in Aqueous Two Phase in Presence of $CO_2$ (Comparative Method of Haberland and Stroh, U.S. Pat. No. 3,013,016)

A mixture of 20 mL $H_2O$ and 500 mL hexane was placed in a flask and purged with a flow of $N_2$. The flask was placed in an ice-bath and a solution of 40 g of $NaBH_4$ in 200 mL of $H_2O$ was added. Purging was continued and 127 g of MTEDA was added. Two phases were present. Carbon dioxide was bubbled through the mixture for ~6 hours with vigorous stirring. At the end of this time, the mixture was allowed to settle for ca. 1 hour. Extraction of the aqueous slurry with 2×100 mL ethyl ether gave a yellow hexane/$Et_2O$ solution which was evaporated to dryness to give about 5 g of a sticky yellow solid (ca. 5% yield).

This Example shows that reduced yields were obtained at the higher water level (compare Example 2). Apparently, the water interfered with the isolation.

In the conventional process of U.S. Pat. No. 3,013,016 conversion of trimethyl and triethylamine to a borane complex could be effected using $CO_2$ in a two phase process. In contrast, the amine borane yield was quite low when a polyamine containing a tertiary nitrogen atom, i.e., methyl-triethylenediamine was used. Lower product yields are believed to be caused in part by inseparability of the product due to solubility of the product in the reaction mixture.

What is claimed is:

1. In a process for producing amine boranes by the reaction of a metal borohydride with a tertiary amine in the presence of an inert organic solvent and a protic acid source, the improvement for enhancing formation of a borane complex of a polyamine containing a tertiary nitrogen atom as the tertiary amine which comprises:

effecting the reaction in the presence of water wherein the water is present in a catalytically effective amount but insufficient for forming two phases.

2. The process of claim 1 wherein the water is present in an amount of from 0.5% based upon the weight of the solvent to the saturation level.

3. The process of claim 2 wherein the acid source is a carboxylic acid wherein the carboxylic acid has from 2-10 carbon atoms.

4. The process of claim 3 wherein said polyamine containing a tertiary nitrogen atom is a cyclized diamine.

5. The process of claim 4 wherein said cyclized/diamine is triethylenediamine or an alkyl derivative thereof.

6. The process of claim 5 wherein said cyclized diamine is methyltriethylenediamine.

7. The process of claim 3 wherein said polyamine is a methylated or ethylated derivative of diethylenetriamine or triethylenetetramine.

8. The process of claim 3 wherein said polyamine is methylated ethylenediamine or methylated propanediamine.

9. The process of claim 2 wherein said acid source is a mineral acid carried in an organic medium and said amine is triethylenediamine or methyltriethylenediamine.

10. A process for forming borane complex of triethylenediamine and methyl-triethylenediamine which comprises reacting methyl-triethyleneamine or triethylenediamine with sodium borohydride in the presence of $C_{2-4}$ carboxylic acid and water wherein the water is provided at a level of from 0.5% by weight of the amine to the saturation level, the reaction being carried out at a temperature from about −25° to 30° C. and a pressure ranging from atmospheric to 50 psig.

11. The process of claim 10 wherein said carboxylic acid is acetic acid.

* * * * *